United States Patent [19]

David et al.

[11] Patent Number: 4,465,660

[45] Date of Patent: Aug. 14, 1984

[54] SUSTAINED RELEASE TABLET CONTAINING AT LEAST 95 PERCENT THEOPHYLLINE

[75] Inventors: Stephen T. David; Dana Brooke; Claude E. Gallian, all of Evansville, Ind.

[73] Assignee: Mead Johnson & Company, Evansville, Ind.

[21] Appl. No.: 451,891

[22] Filed: Dec. 21, 1982

Related U.S. Application Data

[63] Continuation of Ser. No. 249,787, Apr. 1, 1981, abandoned, which is a continuation-in-part of Ser. No. 147,429, May 6, 1980, abandoned.

[51] Int. Cl.$^3$ .......................... A61K 9/20; A61K 9/22; A61K 9/26; A61K 31/52
[52] U.S. Cl. ...................................... 424/15; 424/19; 424/22; 424/253
[58] Field of Search ............................ 424/15, 19-22, 424/253

[56] References Cited

U.S. PATENT DOCUMENTS

| | | | |
|---|---|---|---|
| 2,980,589 | 4/1961 | de Grunigen | 424/362 |
| 3,062,720 | 11/1962 | Costello | 167/82 |
| 3,065,143 | 11/1962 | Christenson et al. | 424/19 |
| 3,079,303 | 2/1963 | Raff et al. | 424/35 |
| 3,080,294 | 3/1963 | Shepard | 167/82 |
| 3,108,046 | 10/1963 | Harbit | 424/38 |
| 3,133,863 | 5/1964 | Tansey et al. | 424/19 |
| 3,147,187 | 9/1964 | Playfair | 424/38 |
| 3,148,124 | 9/1964 | Gaunt | 424/22 |
| 3,279,995 | 10/1966 | Reid | 167/82 |
| 3,279,998 | 10/1966 | Raff et al. | 424/38 |
| 3,344,029 | 9/1967 | Berger | 167/82 |
| 3,402,240 | 9/1968 | Cain et al. | 424/22 |
| 3,424,842 | 1/1969 | Nurnberg | 424/361 |
| 3,456,049 | 7/1969 | Hotko et al. | 424/22 |
| 3,507,952 | 4/1970 | Rednick et al. | 424/22 |
| 3,622,677 | 11/1971 | Short et al. | 424/361 |
| 3,632,778 | 1/1972 | Sheth et al. | 424/361 |
| 3,639,169 | 2/1972 | Broeg et al. | 424/361 |
| 3,641,236 | 2/1972 | Coppen et al. | 424/22 |
| 3,773,920 | 11/1973 | Nakamoto et al. | 424/22 |
| 3,782,993 | 1/1974 | Rothgang et al. | 117/100 A |
| 3,852,421 | 12/1974 | Koyanagi et al. | 424/362 |
| 3,870,790 | 3/1975 | Lowey et al. | 424/19 |
| 3,908,003 | 9/1975 | Hirsh | 424/38 |
| 3,950,508 | 4/1976 | Mony et al. | 424/19 |
| 4,017,598 | 4/1977 | Ohno et al. | 424/362 |
| 4,167,558 | 9/1979 | Sheth et al. | 424/362 |
| 4,209,513 | 6/1980 | Torode et al. | 424/361 |
| 4,215,104 | 7/1980 | Ullman et al. | 424/15 |
| 4,226,849 | 10/1980 | Schor | 424/19 |
| 4,258,027 | 3/1981 | Ullman et al. | 424/15 |
| 4,259,314 | 3/1981 | Lowey | 424/19 |
| 4,264,573 | 4/1981 | Powell et al. | 424/19 |
| 4,361,545 | 11/1982 | Powell et al. | 424/19 |

FOREIGN PATENT DOCUMENTS

10876 5/1980 European Pat. Off. .
55-153715 11/1980 Japan .

OTHER PUBLICATIONS

Lachman et al., The Theory and Practice of Industrial Pharmacy, 2nd Ed., (1976), Lea & Febiger, Philadelphia, PA., pp. 321-358 (Tablets), 439-465, (Sustained Action Dosage Forms).
Chem. Abs. 95:175586j, Benedikt, Asthma-Ther. Theophyllin Optim. Blutspiegel-Bestimm., Arbeitsgespraech, pp. 23-36, (1980).
Chem. Abs. 95:175666k, Sybrecht, Asthma-Ther. Theophyllin Optim. Blutspiegel-Bestimm., Arbeitsgespraech, pp. 108-121, (1980).
Chem. Abs. 94:20311w, Upton et al., J. Pharmacokinet. Biopharm., 8(2), 131-149, (1980).
Chem. Abs. 94:20319e, Upton et al., J. Pharmacokinet. Biopharm., 8(3), 229-242, (1980).
Chem. Abs. 94:90146v, Barrett, Curr. Ther. Res., 28 (5, Sect. 1), 669-681, (1980).
Chem. Abs. 93:12993j, Svedmyr et al., Curr. Med. Res. Opin., 6 (Suppl. 6), 40-44, (1979).
Chem. Abs. 93:12994k, Jonkman et al., Curr. Med. Res. Opin., 6 (Suppl. 6), 71-76, (1979).
Chem. Abs. 93:13041j, Trembath et al., Br. J. Clin. Pharmacol., 9(4), 365-369, (1980).
Chem. Abs. 93:31668y, Lipman, Mod. Med. Asia, 16(2), 59-60, (1980).
Chem. Abs. 93:31686c, French et al., Curr. Med. Res. Opin., 6 (Suppl. 6), 3-13, (1979).

Chem. Abs. 93:245364v, Meyer et al., Chest, 78(2), 300–303, (1980).
Chem. Abs. 92:11154d, Levitt et al., Curr. Ther. Res., 26(3), 311–316, (1979).
Chem. Abs. 92:11163f, Clements, Arch. Pharm. Chemi, Sci. Ed., 7(4), 132–134, (1979).
Chem. Abs. 92:153027p, Sansom et al., Eur. J. Clin. Pharmacol., 16(6), 417–421, (1979).
Chem. Abs. 92:203502n, Nielsen-Kudsk et al., Acta. Pharmacol. Toxicol., 46(3), 205–212, (1980).
Chem. Abs. 91:44449m, Plavsic et al., Lijec. Vjesn., 100(10), 610–612, (1978).
Chem. Abs. 91:78812q, Dasta et al., Am. J. Hosp. Pharm., 36(5), 613–617, (1979).
Chem. Abs. 91:128945h, Apold et al., Lancet, 1(8117), 667–668, (1979).
Chem. Abs. 90:12216w, Weinberger et al., N. Engl. J. Med., 299(16), 852–857, (1978).
Chem. Abs. 88:110416q, Gilenberg, Isr. Pharm. J., 20(5), 254–242, (1977).
Chem. Abs. 88:177130k, Spangler et al., Ann. Allergy, 40(1), 6–11, (1978).
Chem. Abs. 87:111184d, Hendeles et al., Am. J. Hosp. Pharm., 34(5), 525–527, (1977).
Chem. Abs. 87:157084z, Fixley et al., Am. Rev. Respir. Dis., 115 (6, Pt. 1), 955–962, (1977).
Chem. Abs. 87:157116m, Kristofferson et al., Acta. Pharm. Fenn., 86(2), 49–56, (1977).
Chem. Abs. 86:195084m, Kern et al., Drug Intell. Clin. Pharm., 11(3), 144–153, (1977).
Chem. Abs. 85:51681k, Sims et al., Br. J. Clin. Pharmacol., 3(1), 194–196, (1976).
Chem. Abs. 84:111563q, Welling et al., J. Clin. Pharmacol., 16(1), 43–50, (1976).
Chem. Abs. 82:103076b, Mitenko et al., Clin. Pharmacol. Ther., 16(4), 720–726, (1974).
Chem. Abs. 82:103072x, Graham et al., Aust. J. Pharm. Sci., 3(2), 66–68, (1974).

*Primary Examiner*—Shep K. Rose
*Attorney, Agent, or Firm*—Robert H. Uloth; Richard P. Ryan

[57] ABSTRACT

Non-disintegrating theophylline tablets having a pair of opposing substantially planar surfaces and a very thin cross-section have a high bioavailability on ingestion and a relatively steady release rate permitting a 12 hr. dosing interval for maintenance of non-toxic therapeutic blood theophylline concentrations. Excipients or tableting aids are not required, but trace amounts of a tableting lubricant are preferably included to facilitate continuous large scale production.

23 Claims, 7 Drawing Figures

SUSTAINED RELEASE TABLET CONTAINING AT LEAST 95 PERCENT THEOPHYLLINE

REFERENCE TO RELATED APPLICATION

This application is a continuation of application Ser. No. 249,787 filed Apr. 1, 1981 which is a continuation-in-part of application Ser. No. 147,429 filed May 6, 1980, both now abandoned.

DESCRIPTION OF THE PRIOR ART

A number of sustained release theophylline products have been described in the literature and are presently commercially available. They are of two types, hard gelatin capsules, and tablets. The hard gelatin capsule products contain an aggregation of tiny beadlets which are constituted of an edible core such as a non-pariel pellet which is coated with alternating layers of active ingredient and an insoluble delayed release lipid substance. Techniques have been developed for manufacturing beadlets having various drug release rates. By employing various proportions of beadlets having different release rates in a single capsule, a composite release rate of desired duration and magnitude can be obtained. This prior art is not relevant to the present invention, but is of interest as background. It is typified by U.S. Pat. No. 3,080,294 patented Mar. 5, 1963 by Shephard, and U.S. Pat. No. 3,782,993 patented Jan. 1, 1974 by Rothgang, et al., Controlled release tablets have been prepared by tableting aggregates of beadlets of the foregoing type, or by preparing a granulation of coating the individual granules with delayed release coatings of varying release rates. U.S. Pat. No. 3,344,029 patented Sept. 26, 1967 by Berger is representative of this type of sustained release product. Sustained release tablets comprising a fatty or other insoluble matrix in which the drug substance is embedded for slow release are also known. Typical of this type are Cain, et al., U.S. Pat. No. 3,402,240 (September 1968), Costello, U.S. Pat. No. 3,062,720 (November 1962), and Hotko, et al., U.S. Pat. No. 3,456,049 (July 1969).

Tablets and capsules of these types have the disadvantage of requiring rather large amounts of carriers or excipients to effect the release rate. For drugs administered in high dosage amounts and at frequent intervals such as theophylline, a rather large tablet or capsule is necessary, or multiple tablets or capsules for a single dose are required.

U.S. Pat. No. 3,279,995 patented Oct. 18, 1966 by A. F. Reid refers to a shaped pellet having a bi-concave flanged configuration which remains intact during dissolution and affords a substantially uniform surface area throughout the dissolution period. While this principal is involved with the present invention, the intricate shape referred to by Reid is not.

Since a preferred embodiment of the present invention is a shaped tablet comprised almost exclusively of theophylline, applicants have surveyed commercially available controlled release theophylline products, and the literature to ascertain whether any theophylline tablet has been previously described or is in current use which contains little in the way of carriers or excipients. They have found that presently available sustained release theophylline tablets and capsules contain from 17% to 52% by weight of active ingredient and are, thus, clearly distinguished from the preferred products of the present invention. Applicants are unaware of any previous description of the tableting of theophylline by compression without carriers or excipients.

FIELD OF THE INVENTION

The present invention provides a new controlled release theophylline tablet, and the method of maintaining therapeutically effective theophylline blood concentrations in patients undergoing theophylline therapy by oral administration of the tablet at intervals of up to 12 hours during an extended treatment period. The tablet is non-disintegrating in nature so that dissolution takes place solely from the surface and in a preferred form contains in excess of 95% by weight of theophylline.

Theophylline (1,3-dimethylxanthine) has an established role as a bronchodilator and has other therapeutic actions. The drug is rapidly absorbed from the gastrointestinal tract and is readily metabolized and eliminated from the blood. The rate of clearance varies considerably among individuals. Consequently, patients on the usually recommended four times a day dosage regimen using conventional immediate release dosage forms, may exhibit wide variations between the maximal values and the minimal values of theophylline concentrations in their blood which translate into fluctuations in therapeutic benefit as well as incidence of side effects.

Aside from its effects on smooth muscle, theophylline causes stimulation of the central nervous system to produce nervousness and seizures, acts on the kidney to produce diuresis, stimulates the cardiac muscle to increase both rate and force of contraction, and dilates blood vessels. These actions are generally considered to be responsible for the side effects whih may include headache, dizziness, nervousness, nausea, and vomiting, and for some patients militate against use of the drug unless the dosage amount is carefully adjusted.

Serious adverse reactions which involve the cardiovascular system and the central nervous system may occur when blood serum concentrations of theophylline exceed 20 mcg/ml. There is a wide individual variation in the pharmokinetics of theophylline. Elimination half-life of the drug commonly ranges from 3 to 13 hours in normal human subjects. Variation in hepatic enzymes between individuals may account for the variations in theophylline clearance rate. Because of this variability, there is no single dosage that can be recommended for maintenance therapy of all patients, and monitoring of serum theophylline levels is sometimes necessary to accurately individualize the dose.

SUMMARY OF THE INVENTION

It has been found that theophylline in crystalline pulverulent form can be compressed into pharmaceutical tablets without the use of conventional pharmaceutical carriers or tableting aids. A tableting lubricant in an amount of from 0.1% to 0.6% by weight is, however, preferred when a continuous tableting machine run is conducted. The tablets of the present invention have the characteristic of remaining intact during dissolution and of thus dissolving over a rather prolonged period of time rather than in a very short period as is usual with tablets that disintegrate on exposure to a dissolving medium. By presentation of such a non-disintegrating compressed tablet in a configuration whose surface area changes little during dissolution, a sustained release effect is obtained. One such configuration is very thin in cross section and has substantially planar opposing faces large in area relative to the area of the edge walls. It has also been found that with administration of such a tablet delivery of a therapeutic dose of theophylline during a period of from 6 to 12 hours following ingestion is possible. Dumping or immediate release of the dose following ingestion as occurs with a disintegrating tablet does not occur. The present invention thus provides a process for sustaining a relatively constant blood serum level of theophylline within the therapeutic range in a patient requiring theophylline treatment which process involves repeated administration of such a tablet at suitable intervals of up to 12 hrs. The extremes of minimal and maximal blood concentration characterized by the administration of immediate release theophylline dosage forms is avoided.

BRIEF DESCRIPTION OF THE DRAWINGS

FIG. 4 illustrates the top face of the tablet having a logo and two score lines for trisecting of the tablet. FIG. 5 illustrates the lower face of the same tablet having a single score line for bisecting.

DETAILED DESCRIPTION OF THE INVENTION

Figure 1:
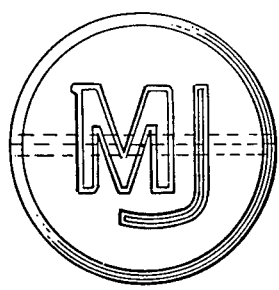
FIGS. 1 and 2 illustrate respectively a top view and a side view of a disc shaped tablet of the present invention having a logo marking on the top face and a score line for bisecting the tablet on the bottom face.
Figure 2:
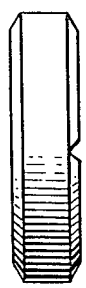
Figure 3:
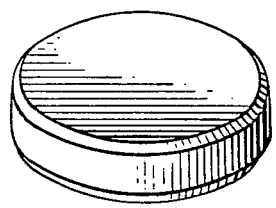
FIG. 3 is a perspective view of a disc shaped tablet of the present invention having no score line or logo.

The compressed pharmaceutical tablet of the present invention contains at least 95% by weight of theophylline and up to 5% by weight of conventional tableting ingredients, but it may consist entirely of theophylline. In one preferred form the sustained release tablet of the present invention contains from 95% to 99.8% by weight of theophylline and the remainder conventional tableting ingredients including at least a tableting lubricant in an amount of from about 0.1% up to about 0.6% by weight. In a preferred form, the tablet contains at least 99% and more preferably from 99.4% to 99.8% by weight of theophylline and a tableting lubricant, preferably magnesium stearate in an amount of 0.1% to 0.6% by weight. The most preferred composition is 99.6% by weight of theophylline and 0.4% by weight of magnesium stearate with no other ingredients being necessary or desirable. Other lubricants such as stearic acid may be employed, but the effect thereof on dissolution characteristics as disclosed herein must be evaluated as shown below.

The tablets of the present invention invention have the characteristic of being non-disintegrating on exposure to a dissolving medium such as water or gastrointestinal fluids. That is, they remain intact during the dissolution period, and the dissolution rate is directly proportional to the surface area of the tablet at any given time during the dissolution period. This results in a relatively steady dissolution of the drug when a tablet shape is selected with changes little in total surface area as the tablet dissolves. The area of a sphere, for instance, changes in proportion to the square of the radius, and therefore exhibits the greatest change in area of any tablet shape during dissolution. Thus, spherical or ovoid shapes approaching the spherical are undesirable for present purposes.

The simplest and preferred form of the present tablet is thin in cross section between relatively large and substantially parallel and planar opposing faces such that the area of the faces is large in comparison to the area of the edge walls. The minimal tablet thickness considering convenience of manufacture and durability, total surface area, and ease of swallowing, is about 0.08 inches. It has been determined empirically that the maximum thickness for such tablet is about 0.12 inches for delivery of a dose of theophylline at a rate to sustain a blood level of from 10-20 mcg/ml on repeated administration. A 500 mg tablet in the form of a disc having a thickness of 0.12 inches has a diameter of about 17/32 inch. Thinner tablets have a greater diameter. This, in part, is the reason why a 300 mg tablet size is preferred since smaller widths and lengths dictated by the constraints on tablet thickness are possible. A tablet thicker than 0.12 inch may exhibit a dissolution rate which changes excessively as dissolution progresses. Also, the dissolution rate of a thicker tablet may be less than required to provide 100% bioavailability. A thin dimension between substantially parallel and planar faces in combination with a non-disintegrating nature characterizes the tablets of the present invention. The preferred tablet thickness is 0.09 to 0.11 inches.

While the preferred embodiment is a thin tablet comprised almost wholly of theophylline as indicated above, it is nevertheless possible to practice the invention with compositions containing somewhat lower proportions of theophylline in combination with conventional tablet ingredients. The additional ingredients are selected to provide a tablet that remains intact during the dissolution period, and thus those materials which cause tablet disintegration such as corn starch or resins or gums which swell on contact with water are to be avoided. Also, those ingredients which rapidly dissolve in water or gastrointestinal fluids are undesirable when used in high proportion since pitting of the tablet surface will occur on exposure to the dissolution medium resulting in an increased rate of dissolution. Excipients of possible utility are glucose, sucrose, lactose, mannitol, and sodium chloride. Insoluble excipients in selected amounts such as calcium phosphate may also be employed.

For a tablet which contains 95% or more of theophylline, tablet hardness does not appear to be relevant to the dissolution characteristics so long as the tablet does not disintegrate while dissolving. Accordingly, any tablet hardness convenient with respect to handling, manufacture, storage, and ingestion in the range of about 8 to 22 SCU is applicable. When using excipients and other tablet ingredients as referred to above in higher proportion tablet hardness may have an effect on the dissolution rate.

Ingredients for inclusion in a tablet according to the present invention are selected empirically by measuring the dissolution characteristics of experimental batches of theophylline tablets containing the various ingredients in the desired proportions, and then modifying the composition ingredient-by-ingredient in stepwise fashion until the desired dissolution characteristics are achieved. This empirical approach to selecting tablet ingredients is described more fully hereinafter.

In the final analysis, a tablet composition is chosen on the basis of the bioavailability of the theophylline contained therein and the blood plasma concentration thereof resulting on repeated administration of a uniform dose at intervals of from 6 to 12 hours, preferably the latter. The target values are absorption of 90% or more of the theophylline contained in an individual tablet within 24 hours following ingestion, and on repeated dosing at intervals of 6 to 12 hours maintenance of a blood serum concentration of theophylline within the therapeutic range. For bronchodilator use the accepted therapeutic blood serum concentration range is about 10 to 20 mcg/ml. Doses of suitable size determined as described below are employed for bronchodilator use on a dosage interval of about 12 hours with adjustment to a shorter interval, if necessary, to afford the desired blood serum concentration.

A preferred configuration contains 300 mg of theophylline in a rectangularly shaped tablet having bisect and trisect scores to provide 2 or 3 subunits of equal size. This is unique in that a single tablet can thus provide dosage units of 100, 150, 200 or 300 mg of theophylline or multiples thereof for convenience in dosage size adjustment. Its sustained release character is not altered by administration as subunits of ⅓, or ½ the original tablet size, and it provides a steady state theophylline blood serum concentration in the generally recommended therapeutic range of 10 to 20 mcg/ml when administered in suitable amount on a twice-a-day schedule (every 12 hours).

FURTHER DETAILED DESCRIPTION OF THE INVENTION

The present invention also provides a method for maintaining a therapeutically effective blood serum concentration of theophylline by repeated oral administration of the foregoing tablet to a patient requiring theophylline therapy during an extended treatment period. The required therapeutically effective blood serum concentration is first ascertained by reference to the practice in the art with respect to the particular disease condition being treated. For bronchodilator use a therapeutically effective blood concentration is generally regarded as 10–20 mcg/ml, but for some patients a therapeutic effect is achieved within the range of 5–10 mcg/ml of theophylline.

Experimental methods are available for determining the rate of theophylline clearance and the plasma half-life values relative to theophylline for individual subjects. Methods are also available to calculate the size of the dosage unit required to establish a given theophylline blood concentration in the patient from the rate of clearance and plasma half-life values. The half-life of theophylline in the blood serum varies among individuals with a wide range having been documented. Representative values are shown in the following table.

| Representative Theophylline Serum Half-Lives | | |
|---|---|---|
| | Half-Life (Hours) | |
| | Mean | Range |
| Adults | | |
| non-smokers | 8.7 | 6.1–12.8 |
| smokers | 5.5 | 4.0–7.7 |
| congestive heart failure | 22.9 | 3.1–82.0 |
| Children (6–16 years) | 3.7 | 1.4–7.9 |

Therapy with theophylline ordinarily takes place over an extended period of from three or four days up to several weeks or months depending upon the patient's condition. In some instances in the treatment of asthma, administration is commenced on the appearance of symptoms and then continued for three or four days after symptoms disappear. In others, dosage may be on a seasonal basis for a period of weeks or months when the exacerbation of symptoms is common.

With the tablet of the present invention the average initial dose for children under 9 years of age is 100 mg of theophylline every 12 hours, e.g. one trisectional portion of a scored 300 mg tablet. For children of ages 9 to 12 years the average initial dose with the theophylline tablet of the present invention is 150 mg of theophylline every 12 hours. For adolescents of ages 12–16 years the average dose is 200 mg ever 12 hours, and for adults 300 mg of theophylline every 12 hours. For those patients who are rapid theophylline metabolizers, such as children of 6–16 years or smokers, the dosage interval may be reduced, for instance to 8 hours. The optimal dosage size and amount can ordinarily be determined by observation of the therapeutic results achieved, and the side effects encountered, or blood serum analyses for theophylline may be made.

Theophylline therapy according to the present invention employing the unique sustained release tablet provided thereby is distinguished from therapy with conventional immediate release theophylline tablets of the prior art by the fact that the required dosage interval during an extended treatment period is usually doubled. This is of great practical benefit because the normal regimen with immediate release tablets requires treatment every six hours which is an inconvenience and impediment to patient compliance. The regimen provided by the present invention permits dosage at 12 hour intervals which not only is a convenience but also an important aid to achieving patient compliance.

DESCRIPTION OF SPECIFIC EMBODIMENTS

Tablet Composition A, Theophylline 99.6% Magnesium Stearate 0.4%—A granulation is prepared by treating 300 g of anhydrous theophylline with 45 ml of water in a mixer followed by drying in a forced air oven at 60° C. until the moisture content is less than 1%. The granulation is then comminuted and blended with 1.2 g of magnesium stearate. The resulting blend is suitable for tableting on a conventional tableting machine to a tablet hardness within the range of from about 7 to 9 SCU. The foregoing batch provides one thousand 300 mg tablets or six hundred 500 mg tablets.

Tablet Composition B, 95.4% Theophylline, 4% Tableting Aids, 0.6% Magnesium Stearate—A granulation is prepared from a dry blend of 500 g of anhydrous theophylline and 10 g of hydroxypropyl methylcellulose (15 cps), with an aqueous solution of 10 g povidone, USP, in approximately 75 ml of water. The granulation is then dried in a forced air oven at 60° C. until the water content is less than 1%. The dried granulation is comminuted, and then blended with magnesium stearate, 3 g. This blended composition is then compressed in a conventional tableting press to provide tablets having a hardness of from 8 to 22 SCU. The batch provides one thousand 500 mg tablets or a greater number of smaller tablets.

In Vitro Dissolution Method—Dissolution Test Method II as described in U.S.P. XIX, 4th Supplement, is convenient for the measurement of the dissolution characteristics of tablets made according to the present invention. Briefly, the method involves placing an individual tablet in 900 ml of water at 37° C. in a 1 liter dissolution kettle bearing a paddle type agitator which is operated at 50 rpm. Aliquots of the dissolution medium are removed at intervals, filtered, and analyzed spectrophotometrically for dissolved theophylline using a wave length of 268 nm, and a standard reference curve prepared by measurement of the absorption of solutions of pure theophylline having various concentrations measured in the same fashion as the test solution.

Bioavailability—An open, single dose, cross-over clinical study employing 12 normal volunteers was employed to determine the bioavailability of various tablets prepared according to the present invention. A commercially available immediate release theophylline product served as reference. Twelve non-smoking male volunteers were selected using the following criteria as grounds for exclusion from the study.
  a. Abnormal pre-treatment hematology, urinalysis, or blood chemistries
  b. Systolic blood pressure greater than 150 mmHg and/or a diastolic blood pressure greater than 100 mmHg
  c. History of severe physical or mental disease
  d. Evidence of gastrointestinal disease (i.e., peptic or duodenal ulcer, colitis, recurrent diarrhea)
  e. History of hepatitis or liver dysfunction
  f. Diabetes mellitus
  g. Thyroid disease
  h. History of seizures
  i. Ingestion of any medication for 7 days prior to the test period, and/or a xanthine containing medication for 15 days prior to the test period
  j. Ingestion of xanthine-containing foods (coffee, tea, chocolate, cola beverages) for 24 hours prior to the test day Subjects fasted from bedtime of the night prior to the test day until after the 4 hr blood sample had been withdrawn. A light meal without coffee, tea, chocolate, cola beverages, butter or cream was eaten after the 4 hr sample, and again between the 10 hr and 12 hr sample collections. Participants presented to the testing unit prior to 6:00 p.m. on the day before the test day for domiciling over the next 32 hours.

A single dose of one of the test tablets was administered to the subject with 100 ml of water at 8:00 a.m. of the test period. For each subject a crossover test period with the immediate release theophylline reference standard was employed. Test periods were separated by periods of one week. Blood samples of sufficient volume to deliver 5 ml of plasma were drawn immediately prior to drug administration and at ¼, ½, 1, 2, 3, 4, 5, 6, 7, 8, 10, 12, 16, and 24 hours thereafter. Plasmas were analyzed for theophylline by the high pressure liquid chromatographic method of Weddele and Mason, J. Pharm. Sci., 1976 65:856. A graph was prepared of plasma theophylline concentration versus time. Areas under the curves extrapolated to infinity were determined by a standard mathematical method, and were used to calculate percentage bioavailability by comparison of the area under the curve for a test tablet with that of the immediate release reference standard.

In vitro dissolution and bioavailabilities were determined according to the foregoing methods for four disc-shaped tablets and one rectangular tablet having the compositions shown in the following table where the results are arranged. Dissolution data for a second similar rectangular tablet are also shown in the table.

| | | | | In Vitro Dissolution and Bioavailability | | | | | | |
|---|---|---|---|---|---|---|---|---|---|---|
| Tablet No. | Composition | Theophylline Amount | Tablet Thickness (inches) | Tablet Diameter (inches) | Dissolution (%) Hours | | | | | Bioavailability (% in 24 hrs.) |
| | | | | | 0.5 | 1.0 | 2.0 | 4.0 | 6.0 | |
| 051 | A | 500 mg | 0.150 | 15/32 | 15 | 28 | 50 | 80 | — | 76 |
| 181 | A | 300 mg | 0.103 | 7/16 | — | 32 | 55 | 83 | 93 | 106 |
| 191 | A | 300 mg | 0.087 | 15/32 | — | 33 | 57 | 86 | 94 | 93 |
| 201 | A | 300 mg | 0.100 | * | 30 | 45 | 73 | 95 | — | 96 |
| 202 | A | 300 mg | 0.100 | + | 24 | 43 | 74 | 94 | — | — |
| 111 | B | 500 mg | 0.15 | 15/32 | 25 | 45 | 75 | 95 | — | 86 |

Figure 4:
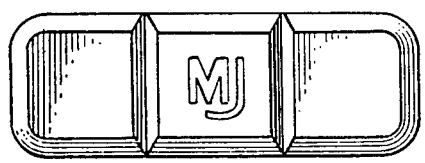
FIGS. 4, 5 and 6 are, respectively, a top view, a bottom view, and an end view of a rectangular tablet of the present invention.
Figure 5:
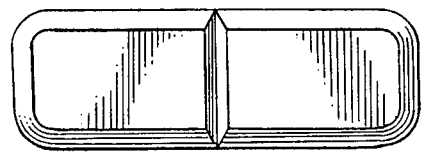
Figure 6:
Figure 7:
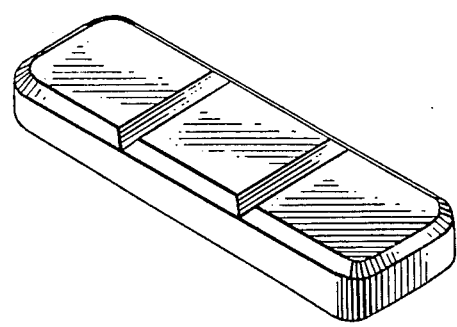
FIG. 7 is a perspective view of a tablet similar to that illustrated in FIG. 4 except that no logo is present on the top face.

*Rectangular in shape; length 0.660 in., width 0.230 in.; bisect scores on side walls; trisect scores on opposing faces.
+Rectangular in shape; length 0.640 in., width 0.250 in.; bisect score on one planar face, and trisect scores on opposing planar face as illustrated in FIGS. 4, 5, and 7.

Tablet 051 having a thickness of 0.15 inches but otherwise conforming to the present invention was found to have a bioavailability of 76% that of a conventional immediate release tablet. Modification of the composition of this tablet by inclusion of a small quantity of hydroxypropyl methylcellulose as a tablet disintegrant and povidone as a granulation ingredient as shown in tablet 111 resulted in a bioavailability of 86%. Each of tablets 181, 191 and 201 had the same composition but different tablet shapes and thicknesses as shown in the table. Each exhibited a bioavailability in excess of 90%. These tablets and tablet 202 constitute preferred embodiments of the present invention.

It is significant and surprising to note that tablet 201, a rectangular tablet having opposing bisect scores on the edge walls and opposing trisect scores on the planar faces, exhibited substantially the same in vitro dissolution rate as indicated in the foregoing table whether the intact tablet, the bisected tablet, or the trisected tablet was employed for the measurement. While co-pending application Ser. No. 024,139 filed Mar. 26, 1979 and now U.S. Pat. No. 4,215,104 patented July 29, 1980 discloses rectangular tablets scored on different faces for optional bisecting, or trisecting by manual breaking, there is no suggestion in that patent that such a design would be suitable for a controlled release tablet. However, within the narrow constraints of the present invention, trisecting or bisecting of a theophylline tablet containing from 100 to 500 mg thereof, having substantially planar faces, and a thickness of from 0.08 to 0.12 inches has no practical effect on the dissolution rate. The entire disclosures of application Ser. No. 024,139 cited above, and of related application Ser. No. 121,615 filed Feb. 14, 1980 and now U.S. Pat. No. 4,258,027 patented Mar. 24, 1981 are incorporated herein by reference.

Screening of Tablet Ingredients—Tablets were prepared as described above for Composition A but containing varying amounts of magnesium stearate; and 250 mg of anhydrous theophylline. The tablets were disc-shaped, 13/32 inches in diameter and 0.10 inches thick.

The in vitro dissolution values for each was determined as described above, and the results obtained are shown in the following table.

Effect of Magnesium Stearate on Dissolution

| Magnesium Stearate (% by wt.) | Percent Dissolved | | | | | | |
|---|---|---|---|---|---|---|---|
| | 0.5 hr | 1 hr | 2 hr | 3 hr | 4 hr | 5 hr | 6 hr |
| None | 28.4 | 51.5 | 82.2 | 93.7 | 95.3 | — | — |
| 0.3 | 22.2 | 41.1 | 70.1 | 86.1 | 93.8 | 94.5 | 95.8 |
| 0.4 | 20.0 | 36.4 | 62.3 | 80.1 | 89.9 | 95.7 | 97.0 |
| 0.5 | 20.0 | 34.4 | 58.9 | 75.2 | 84.7 | 91.4 | 94.9 |
| 0.8 | 14.7 | 25.0 | 41.6 | 54.3 | 64.4 | 71.8 | 78.9 |

It is evident that increasing the proportion of magnesium stearate retards the rate of dissolution of the tablet. While the dissolution rates obtained for the foregoing tablets except that containing 0.8% by weight of magnesium stearate were acceptable, the preferred range of 0.3% to 0.5% of magnesium stearate, and the most preferred proportion of 0.4% was selected.

The foregoing method for evaluating the effect of magnesium stearate on the dissolution characteristics of the resulting tablet can be applied to the screening of other tablet ingredients which it may be desired to include in a tablet prepared according to the present invention. Those ingredients are selected which provide a tablet conforming to the following dissolution (percent dissolved) criteria using the test described above: 0.5 hr, up to 35%; 1.0 hr, 30–54%; 2 hr, 55–89%; and 4 hr, 83–100%. Preferred dissolution criteria are: 0.5 hr, up to 40%; 1.0 hr, 35–60%; 2 hr, at least 60%; and 4 hr, at least 85%.

FURTHER DESCRIPTION OF SPECIFIC EMBODIMENTS

A batch of tablets prepared as described above for Tablet Composition A, Theophylline 99.6%, Magnesium Stearate 0.4%, was found to have a slightly slower dissolution rate at the 4-hour interval, 79.9%, relative to the 4-hour target value referred to above, 83–100%. A number of these tablets were comminuted through an appropriate mill. Two portions of the ground powdered tablets were then diluted with theophylline containing no additional magnesium stearate as lubricant in the proportion of 1 part by weight of ground powdered tablets to 1 or 2 parts by weight of unlubricated theophylline. These blends produced rectangular tablets when compressed as described above containing 0.2 and 0.13% magnesium stearate respectively by weight. A portion of the ground tablets without added theophylline was also tableted. The dissolution properties of these three batches of tablets were then determined according to the method referred to above with the following results.

Dissolution of 300 mg Controlled Release Theophylline Tablets Containing Low Levels of Magnesium Stearate

| | Dissolution, % Dissolved (Avg. 6 Tabs) | | | | |
|---|---|---|---|---|---|
| | 0.5 | 1.0 | 2.0 | 3.0 | 4.0 |
| Original tablets[1] | 20.9 | 35.6 | 56.4 | — | 79.9 |
| Ground and recompressed tablets[1] | 19.0 | 30.4 | 46.9 | — | 68.7 |
| Ground, diluted 1:1 and recompressed tablets[2] | 23.4 | 39.8 | 63.1 | — | 91.5 |
| Ground, diluted 1:2 and recompressed tablets[3] | 28.9 | 50.7 | 78.6 | 96.1 | 102.5 |

[1]0.4% magnesium stearate
[2]0.2% magnesium stearate
[3]0.13% magnesium stearate The results show that retableting undiluted ground tablets retarded the dissolution rate. Diluting of the ground tablets with unlubricated theophylline followed by retableting increased the rate of dissolution. The ground, diluted and recompressed tablets containing 0.13% and 0.2% by weight of magnesium stearate were well within the target dissolution limits referred to above.

Bioavailability, Multiple-Dose Study—Controlled release tablets of the present invention (designated Product B for this study) having the composition and shape of tablet No. 202 referred to in the first of the foregoing tables were compared for their bioavailability on multiple dosing to an immediate release commercial theophylline tablet (designated Product A for this study). The multiple dose study was conducted according to a two-period, randomized cross-over, open label design and employed 18 normal volunteers. Each volunteer was evaluated with a physical examination, medical history, complete blood chemistry (including differential white cell count and standard medical analysis-12) and urinalysis. Only these volunteers were accepted for the study who conformed to the following criteria.

a. Non-smoking male subjects between the ages of 21 and 40 years.
b. In excellent health on the basis of history, physical examination, and the above described tests.
c. No history of drug or alcohol abuse.
d. Plasma theophylline clearance greater than or equal to 2.7 L./hr. and plasma half-life less than or equal to 9 hrs as determined in the preliminary test dose phase of the study described below.
e. Weight between 140 and 200 pounds and within ±10% of normal weight for height.
f. No theophylline-containing medication to have been take for 15 days prior to the study and no other medication of any kind for 7 days prior to the study.

Dosage was individualized for each subject in a preliminary test dose phase in which the clearance rate and half-life of theophylline in the blood plasma following a single dose was determined. A single oral 400 mg dose of Product A was taken at about 8:00 a.m. after fasting for 12 hrs. The medication was swallowed with 100 ml of water and no chocolate, tea, coffee, coca-cola or other caffeine containing food or beverage was permitted for 24 hrs before or 24 hrs after the test dose. The subjects fasted for 2 hrs after the test dose and 5 ml blood samples were collected just prior to swallowing the test dose and 0.5, 1, 2, 3, 4, 5, 7, 9, 12 and 24 hrs after the test dose. Plasma theophylline levels were measured from each of these samples and the data were used to determine the clearance rates and the plasma half-life values. The appropriate test dose for each subject to provide a mean steady state plasma concentration of 13 mcg/ml and a peak plasma concentration of 15 mcg/ml was then calculated. The following table contains clinical information for each of the 18 participants including the dosage size determined for use in the multiple dose phase of study and a notation as to adverse drug reactions observed.

Clinical Information For 18 Participants

| Number | Age | Height (in) | Weight (kg) | Sequence* | Dose Treatment A qid | Dose Treatment B bid | Adverse Drug Reactions Treatment A | Adverse Drug Reactions Treatment B |
|---|---|---|---|---|---|---|---|---|
| 1 | 22 | 76 | 90.0 | AB | 250 | 500 | No | No |
| 2 | 22 | 70 | 75.0 | BA | 300 | 600 | No | Nausea, headache |
| 3 | 22 | 72 | 68.2 | AB | 250 | 500 | Headache | No |
| 4 | 22 | 73 | 77.3 | BA | 250 | 500 | Headache | No |
| 5 | 23 | 72 | 72.7 | BA | 300 | 600 | No | Headache |
| 6 | 23 | 71 | 77.3 | AB | 300 | 600 | No | No |
| 7 | 25 | 73 | 80.0 | BA | 250 | 500 | No | No |
| 8 | 23 | 69 | 68.5 | B discontinued | — | 600 | — | Nausea, Headache |
| 9 | 22 | 71 | 79.5 | BA | 300 | 600 | No | Nausea, Headache |
| 10 | 22 | 67 | 68.2 | AB | 200 | 400 | No | No |
| 11 | 22 | 71 | 79.5 | AB | 300 | 600 | No | Headache |
| 12 | 25 | 72 | 80.5 | AB | 200 | 400 | No | No |
| 13 | 25 | 72 | 72.7 | AB | 250 | 500 | Nausea, Headache | No |
| 14 | 23 | 71 | 77.7 | BA | 300 | 600 | No | No |
| 15 | 22 | 70 | 72.7 | BA | 300 | 600 | No | No |
| 16 | 22 | 66 | 68.2 | BA | 250 | 500 | No | No |
| 17 | 22 | 69 | 65.9 | A discontinued | 250 | — | Nausea, Headache | — |
| 18 | 24 | 74 | 84.1 | AB | 200 | 400 | No | No |

*Treatment A: Commercial immediate release tablet
Treatment B: Tablet No. 202

The subjects were then assigned to one of two equal sized groups using a randomization schedule. One group received Product A on a dosage schedule for days 1 through 4 involving taking their medication orally at 8:00 a.m., 2:00 p.m., 8:000 p.m. and 2:00 a.m. and at 8:00 a.m. on day 5. Thos receiving Product B took their medication orally at 8:00 a.m. and 8:00 p.m. on days 1 through 4 and at 8:00 a.m. only on day 5. No medication was administered on days 6 and 7 which served for wash-out of the prior medication, and then each participant was switched to the other test product which was administered according to the foregoing every six hour or every twelve hour schedule as appropriate. All doses of medication were swallowed with 100 ml of water. Blood samples were collected as shown in the following table. In each instance the 8 a.m., 2 p.m., and 8 p.m. samples were taken prior to medication.

Blood Sample Schedule

| Product | Day | a.m. | p.m. |
|---|---|---|---|
| A | 3 | 8, 2 | 8 |
| | 4 | 8, 9, 10, 11, 12 | 2, 8 |
| | 5 | 8, 9, 10, 11, 12 | 2, 4, 6, 8 |
| | 6 | 8, 12 | 8 |
| B | 3 | 8 | 8 |
| | 4 | 8, 9, 10, 11, 12 | 2, 4, 6, 8 |
| | 5 | 8, 9, 10, 11, 12 | 2, 4, 6, 8 |
| | 6 | 8, 10, 12 | 2, 4, 6, 8 |

Plasma theophylline concentrations were determined by assay and the results shown in the following table were calculated.

Multiple Dose Bioavailability of Theophylline From Sustained Release (Product B) and Immediate Release Tablets (Product A) at Steady State

| Product | No. of Subjects | Avg. Total Daily Dose (mg) | Dosing Intervals (hours) | AUC* (hrs.mg/L) | % Bio-available | $Cp_{ss}$* ($\mu$g/ml) | $C_{max}$* ($\mu$g/m) | $C_{min}$* ($\mu$g/ml) | $C_{max}$-$C_{min}$* ($\mu$g/ml) | $T_{max}$* (min) |
|---|---|---|---|---|---|---|---|---|---|---|
| B | 16 | 1050 | 12 | 151 ±26 | 98 | 12.55 | 15.8 ±2.6 | 8.77 ±1.82 | 7.07 ±1.97 | 235.0 ±68.8 |
| A | 16 | | 6 | 156 ±30 | 100 | 13.04 | 15.9 ±3.2 | 10.3 ±2.2 | 5.61 ±2.2 | 95.4 ±39.1 |

*AUC - area under the plasma concentration curve
$CP_{ss}$ - mean steady-state plasma concentration
$C_{max}$ - mean maximal plasma concentration
$C_{min}$ - mean minimal plasma concentration
$C_{max}$-$C_{min}$ - mean plasma concentration swing
$T_{max}$ - mean time to maximal concentration Data for only 16 of the 18 subjects were employed since two subjects, one having Product A and the other Product B, discontinued the study because of headache or nausea.

Dosing with the sustained release tablet of the present invention (Product B) every 12 hours resulted in approximately the same mean steady state and maximal plasma theophylline concentrations as did dosing with the commercial immediate release preparation (Product A) at 6 hr intervals. A greater difference between the maximal and minimal plasma concentrations was observed with Product B but this difference was not deemed to be large enough to effect the clinical performance. The areas under the plasma concentration versus time curves and the maximal theophylline concentrations observed in the blood plasma for each treatment were not statistically different. The results of this study clearly show that when Product B of the present invention when administered on a 12 hr dosage schedule results in plasma theophylline concentrations comparable to those obtained with Product A, a commercial immediate release preparation when administered on a 6 hr dosage schedule. The plasma theophylline concentrations achieved are within the generally recommended therapeutic range of 10–20 mcg/ml. To further illustrate this latter point the mean theophylline plasma concentration values achieved at the various time intervals following the morning dose on days 4 and 5 (steady-state conditions) with the present sustained release tablet (Product B) are shown in the following table.

| Hours Following 8 a.m. Dose | Mean Theophylline Plasma Conc. (mcg/ml) | |
| --- | --- | --- |
|  | Day 4 | Day 5 |
| 0 | 10.8 | 10.0 |
| 1 | 11.8 | 11.5 |
| 2 | 13.4 | 12.9 |
| 3 | 14.8 | 14.6 |
| 4 | 15.6 | 15.0 |
| 6 | 14.8 | 13.9 |
| 8 | 13.2 | 11.8 |
| 10 | 11.2 | 10.2 |
| 12 | 9.5 | 8.6 |

The higher values at 0 time (before the 8 a.m. dose) appear to reflect a diurnal variation in the elimination of theophylline by the body.

What is claimed is:

1. A sustained release pharmaceutical tablet comprising 95% to 99.8% by weight of theophylline, and the remainder conventional pharmaceutical tablet ingredients selected to provide a tablet that remains intact during dissolution, said tablet having a pair of substantially planar opposing faces joined by edge walls and a thickness of from 0.08 to 0.12 inches which when administered to a human in a therapeutically effective amount at consecutive 12 hour intervals affords a continuous blood serum concentration of from 10 mcg/ml to 20 mcg/ml of theophylline during said intervals and wherein said tablet has a bisect score on one of said planar faces and a pair of trisect scores on the opposing planar face.

2. The pharmaceutical tablet of claim 1 containing 100 mg to 500 mg of theophylline.

3. The pharmaceutical tablet of claim 1 having a thickness of 0.09 to 0.11 inches.

4. The pharmaceutical tablet of claim 1 containing from 0.2% to 0.6% by weight of magnesium stearate as tableting lubricant.

5. The pharmaceutical tablet of claim 1 containing 0.3% to 0.5% by weight of magnesium stearate as tableting lubricant.

6. The pharmaceutical tablet of claim 1 consisting essentially of 99.6% by weight of theophylline and 0.4% by weight of magnesium stearate.

7. The pharmaceutical tablet of claim 6 containing 300 mg of theophylline.

8. The pharmaceutical tablet of claim 7 wherein said edge walls define a rectangle.

9. A sustained release pharmaceutical tablet consisting essentially of 99.4% to 99.8% by weight of theophylline and 0.1% to 0.6% by weight of a tableting lubricant selected to provide a tablet that remains intact during dissolution, said tablet having a pair of substantially planar opposing faces joined by edge walls and a thickness of from 0.08 to 0.12 inches which when administered to a human in a therapeutically effective amount at consecutive 12 hour intervals affords a continuous blood serum concentration of from 10 mcg/ml to 20 mcg/ml of theophylline during said intervals and wherein said tablet has a bisect score on one side of said planar faces and a pair of trisect scores on the opposing planar face.

10. The tablet of claim 9 where the tableting lubricant is magnesium stearate.

11. A pharmaceutical tablet for the maintenance of a therapeutically effective blood concentration of theophylline during a dosage interval of up to 12 hours following ingestion thereof in therapeutically effective amount comprised of at least 95% by weight of theophylline and the remainder conventional pharmaceutical tablet ingredients selected to provide a tablet which dissolves without first disintegrating when contacted with water during a period of about 4 hours to the extent of from 83% to 100% by weight, wherein said tablet has a pair of substantially planar opposing faces joined by edge walls and a thickness of from 0.08 to 0.12 inches and the therapeutically effective theophylline blood serum concentration maintained by said tablet is substantially within the range of from about 10 mcg/ml to 20 mcg/ml and wherein said tablet has score lines arranged for both bisecting and trisecting the tablet.

12. The pharmaceutical tablet of claim 11 containing from about 100 mg to 500 mg of theophylline.

13. The pharmaceutical tablet of claim 11 which when administered to a human in bronchodilative effective amount at consecutive intervals of from about 8 to 12 hours maintains a bronchodilative effective blood serum concentration of theophylline during said interval.

14. The pharmaceutical tablet of claim 11 having a thickness of 0.09 to 0.11 inches.

15. The pharmaceutical tablet of claim 11 containing at least 99% by weight of theophylline and a tableting lubricant.

16. The pharmaceutical tablet of claim 15 containing from 0.1% to 0.6% by weight of magnesium stearate as tableting lubricant.

17. The pharmaceutical tablet of claim 15 containing from 0.3% to 0.5% by weight of magnesium stearate as tableting lubricant.

18. The pharmaceutical tablet of claim 11 consisting essentially of 99.6% by weight of theophylline and 0.4% by weight of magnesium stearate.

19. The pharmaceutical tablet of claim 11 containing 300 mg of theophylline.

20. The pharmaceutical tablet of claim 11 having a bisect score line on one of said planar faces and a pair of trisect score lines on the opposing planar face.

21. The pharmaceutical tablet of claim 11 wherein said edge walls define a rectangle.

22. The pharmaceutical tablet of claim 11 wherein said tablet consists essentially of 99.4% to 99.8% by weight of theophylline and 0.1% to 0.6% by weight of magnesium stearate.

23. The pharmaceutical tablet of claim 21 having a thickness of 0.1 inches.

* * * * *